United States Patent
Ryu (12)

(10) Patent No.: US 7,856,260 B1
(45) Date of Patent: Dec. 21, 2010

(54) IMPLANTABLE CARDIAC PATCH FOR MEASURING PHYSIOLOGIC INFORMATION

(75) Inventor: Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 1139 days.

(21) Appl. No.: 11/470,557

(22) Filed: Sep. 6, 2006

(51) Int. Cl.
A61B 5/042 (2006.01)
A61N 1/05 (2006.01)

(52) U.S. Cl. .................. 600/375; 600/374; 607/129; 607/130

(58) Field of Classification Search ........... 600/374, 600/375; 607/129, 130
See application file for complete search history.

(56) References Cited

U.S. PATENT DOCUMENTS

| | | | | |
|---|---|---|---|---|
| 4,628,937 | A | * | 12/1986 | Hess et al. ............. 600/374 |
| 5,095,916 | A | * | 3/1992 | Smits ................. 607/116 |
| 5,158,092 | A | * | 10/1992 | Glace ................. 600/518 |
| 5,476,503 | A | | 12/1995 | Yang |
| 5,509,924 | A | | 4/1996 | Paspa et al. |
| 5,849,033 | A | * | 12/1998 | Mehmanesh et al. ....... 607/129 |
| 6,009,349 | A | | 12/1999 | Mouchawar et al. |
| 2002/0082647 | A1 | | 6/2002 | Alferness et al. |
| 2002/0115939 | A1 | | 8/2002 | Mulligan et al. |
| 2003/0199955 | A1 | | 10/2003 | Struble et al. |
| 2005/0027320 | A1 | | 2/2005 | Nehls et al. |
| 2005/0102010 | A1 | | 5/2005 | Lau et al. |
| 2005/0102011 | A1 | | 5/2005 | Lau et al. |
| 2005/0102012 | A1 | | 5/2005 | Lau et al. |
| 2005/0102013 | A1 | | 5/2005 | Lau |
| 2005/0102014 | A1 | | 5/2005 | Lau et al. |
| 2005/0102015 | A1 | | 5/2005 | Lau et al. |
| 2005/0119717 | A1 | | 6/2005 | Lau et al. |
| 2005/0137673 | A1 | | 6/2005 | Lau et al. |
| 2005/0171589 | A1 | | 8/2005 | Lau et al. |
| 2005/0288715 | A1 | | 12/2005 | Lau et al. |
| 2006/0009675 | A1 | | 1/2006 | Meyer |
| 2006/0009831 | A1 | | 1/2006 | Lau et al. |

FOREIGN PATENT DOCUMENTS

| | | |
|---|---|---|
| WO | 2005046789 A1 | 5/2005 |
| WO | 2005092431 A1 | 10/2005 |

OTHER PUBLICATIONS

NonFinal Office Action, mailed May 1, 2009: Related U.S. Appl. No. 11/470,564.
NonFinal Office Action, mailed Dec. 8, 2009—Related U.S. Appl. No. 11/470,564.

* cited by examiner

*Primary Examiner*—Lee S Cohen (57) ABSTRACT

An implantable cardiac patch is configured to be joined to a surface of a heart and includes a body portion having an inner surface configured to be joined to the surface of the heart. The body portion also has a plurality of pores extending into the body portion from the inner surface. A plurality of electrodes are attached to the body portion such that the electrodes are positioned proximate the surface of the heart, and a lead is electrically connected to the electrodes at a connecting portion of the lead. The lead has a proximal end configured for joining to an implantable device.

17 Claims, 6 Drawing Sheets

IMPLANTABLE CARDIAC PATCH FOR MEASURING PHYSIOLOGIC INFORMATION

CROSS-REFERENCE TO RELATED APPLICATIONS

This application is related to copending U.S. patent application Ser. No. 11/470,564, titled "Method and Apparatus for Measuring Physiologic Information Utilizing an Implantable Device".

BACKGROUND OF THE INVENTION

Embodiments of the present invention pertain generally to methods and systems for measuring physiologic information utilizing an implantable cardiac patch for the early detection and prevention of congestive heart failure.

In the United States, it is estimated that approximately five million people have congestive heart failure ("CHF"). CHF is the inability of the heart to provide sufficient blood flow to meet the body's demand for oxygen. Patients suffering from CHF may also have associated cardiac diseases such as myocardial ischemia, which if prolonged lead to myocardial infarctions and life-threatening arrhythmias. Thus, it is desirable to be able to monitor and treat the local as well as global status of the heart.

A review of the cardiac conduction system is provided as background. A normal heartbeat occurs through an orderly deployment of electrical charge through the myocardium resulting in the contraction of the atrium followed by the contraction of the ventricles. The cardiac conduction system coordinates the depolarization of the heart. The heart includes a group of cells called the sinoatrial node ("SA node"), located in the atrium that initiate a heartbeat. Depolarization spreads radially through the atrium via atrial pathways to the atrioventricular node ("AV node"). Atrial depolarization may be complete in about 0.1 seconds. Propagation through the AV node takes place slowly to allow the atria to empty and the ventricles to fill with blood. This slow conduction in the AV node results in a delay (e.g. around 0.1 s) between atrial and ventricular excitation. When the depolarization arrives at the ventricles, a bundle of HIS spreads the excitation through the Purkinje system to the right and left ventricles at a relatively high velocity (e.g. 1-2 m/s). The wave of depolarization is rapidly conducted through the Purkinje fibers to all parts of the ventricles (e.g. in about 0.08-0.1 seconds). The timing of the heart's depolarization facilitates filling of the ventricles from atrial contraction prior to ventricular contraction. The cardiac conduction system provides the ability of the heart to have a rate and rhythm to provide the required blood flow to the body.

Myocardial Infarction ("MI") occurs when the blood supply to parts of the myocardium is interrupted leading to the death of cardiac muscle cells. MIs are often complicated by serious arrhythmias. An arrhythmia occurs when a disease or an abnormality in the electrical pathway of the heart causes the normal cardiac rhythm, called sinus rhythm, to be disrupted. Patients with chronic myocardial infarction are at most risk of ventricular tachycardia ("VT"). Persistent VT leads to ventricular fibrillation ("VF"), where a part of the ventricular muscle fibers are depolarized and parts are completely repolarized. Multiple areas of the ventricles attempt to control the heart's rhythm resulting in the fibrillating ventricles inability to pump blood effectively. If not terminated and effectively treated, VF causes the blood circulation to stop, leading to cardiac arrest and death.

Standard medical treatments have been developed to treat heart disease. Historically, congestive heart failure has been managed by treating the patient with drugs, pacemakers and the like. Also, devices have been proposed to improve cardiac output such as left ventricular assist pumps and multi-chamber pacing to improve cardiac output. Electrocardiograms ("ECG") have been used for detecting arrhythmias. In addition, cardiac harnesses have been employed to compress the heart and provide an electrical shock for defibrillation. Other devices such as implantable cardioverter defibrillators (ICDs) have been used to electrically shock the heart back to a normal cycle and to terminate most tachyarrhythmias, including atrial tachycardia ("AT"), VT and VF. An ICD typically has a lead from the ICD connected to the right ventricle and is used to detect both bradyarrhythmia and tachyarrhythmia. ICD therapy is usually prescribed to patients that have had one episode of VT/VF or suffered cardiac arrest. The ICD delivers an electric shock to depolarize the entire myocardium simultaneously in order to restore a normal rate and rhythm to the heart. One difficulty with current ICD therapies, especially in patients who have had an MI, is that there is no satisfactory method to reduce scar formation and myocardial wall thinning.

Recently, an epicardial mesh/patch has been proposed for use with the ICD that is inserted into the pericardial spaced and placed on the epicardium of the atrium or ventricle. The mesh/patch can be placed during open heart surgery or by minimally invasive intrapericardial lead placement techniques via the subxiphoid access. However, conventional epicardial mesh/patches are unable to detect deflections of the tissue as the heart is depolarized. Because of the anatomical difference of the atria and the ventricles, the sequential activation, depolarization, and repolarization of the atria and ventricles produce differentiable deflections. Thus, conventional ICDs are not able to detect an arrhythmia before it fully develops and similarly are unable to save cardiac tissue from being damaged. Furthermore, conventional implantable devices (e.g. ICD, pacemaker or otherwise) are unable to detect a MI in patients who have already suffered a MI.

A need remains, especially for patients who have recently suffered a myocardial infarction, for an implantable device that affords early detection of abnormal ventricular activation in order to prevent reentrant VT from occurring. This, in turn, may also prevent the occurrence of life-threatening VF that often follows VT.

A need remains for an improved cardiac patch that is directed to overcoming one or more of the problems set forth above. A need remains for an improved mesh/patch and implantable device having the ability to monitor myocardial deflections, sense abnormal heart rhythm, applying preventative pacing schemes during the early stages of MI, and measure the excitability of tissue and the tissue's response to various pacing schemes.

BRIEF SUMMARY

In one aspect, an implantable cardiac patch is provided that is configured to be joined to a surface of a heart. The cardiac patch includes a body portion having an inner surface configured to be joined to the surface of the heart. The body portion also has a plurality of pores extending into the body portion from the inner surface. A plurality of electrodes are attached to the body portion such that the electrodes are positioned proximate the surface of the heart, and a lead is electrically connected to the electrodes at a connecting portion of the lead. The lead has a proximal end configured for joining to an implantable device.

In another aspect, an implantable detection and therapy delivery system is provided including a cardiac patch having a body portion with an inner surface configured to be joined to the surface of the heart and a plurality of pores extending into the body portion from the inner surface. The cardiac patch also includes a plurality of electrodes attached to the body portion such that the electrodes are positioned proximate the surface of the heart. The electrodes measure electrical characteristics of the heart indicative of a present physiologic state of a portion of the heart disposed proximate to the electrodes. The system also includes a lead electrically connected to the electrodes and configured to relay signals relating to the electrical characteristics, and an implantable device electrically connected to the lead and configured to receive the relayed signals. The implantable device compares the electrical characteristics measured by at least one combination of the electrodes to obtain a measured characteristic value.

In a further aspect, a cardiac patch system is provided that is configured to be joined to a surface of a heart. The system includes a pericardial lead having a lead body extending between a distal end and a proximal end. The distal end engages the surface of the heart and the proximal end is configured to be electrically connected to an implantable device. The lead further includes at least one lead electrode embedded within the lead body proximate to the distal end. The lead electrode is configured to receive pacing signals for pacing the heart from the implantable device, wherein the pacing signals are received from the implantable device based on a predetermined pacing scheme. The system also includes a cardiac patch connected to the pericardial lead remote from the distal end and remote from the proximal end. The patch includes a body portion having an inner surface configured to be joined to the surface of the heart, and the body portion has a plurality of pores extending into the body portion from the inner surface. The patch also includes a plurality of patch electrodes attached to the body portion such that the patch electrodes are positioned proximate the surface of the heart. The patch electrodes are configured to be electrically connected to the implantable device.

DETAILED DESCRIPTION

In the following detailed description, reference is made to the accompanying drawings which form a part hereof, and in which is shown by way of illustrating specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
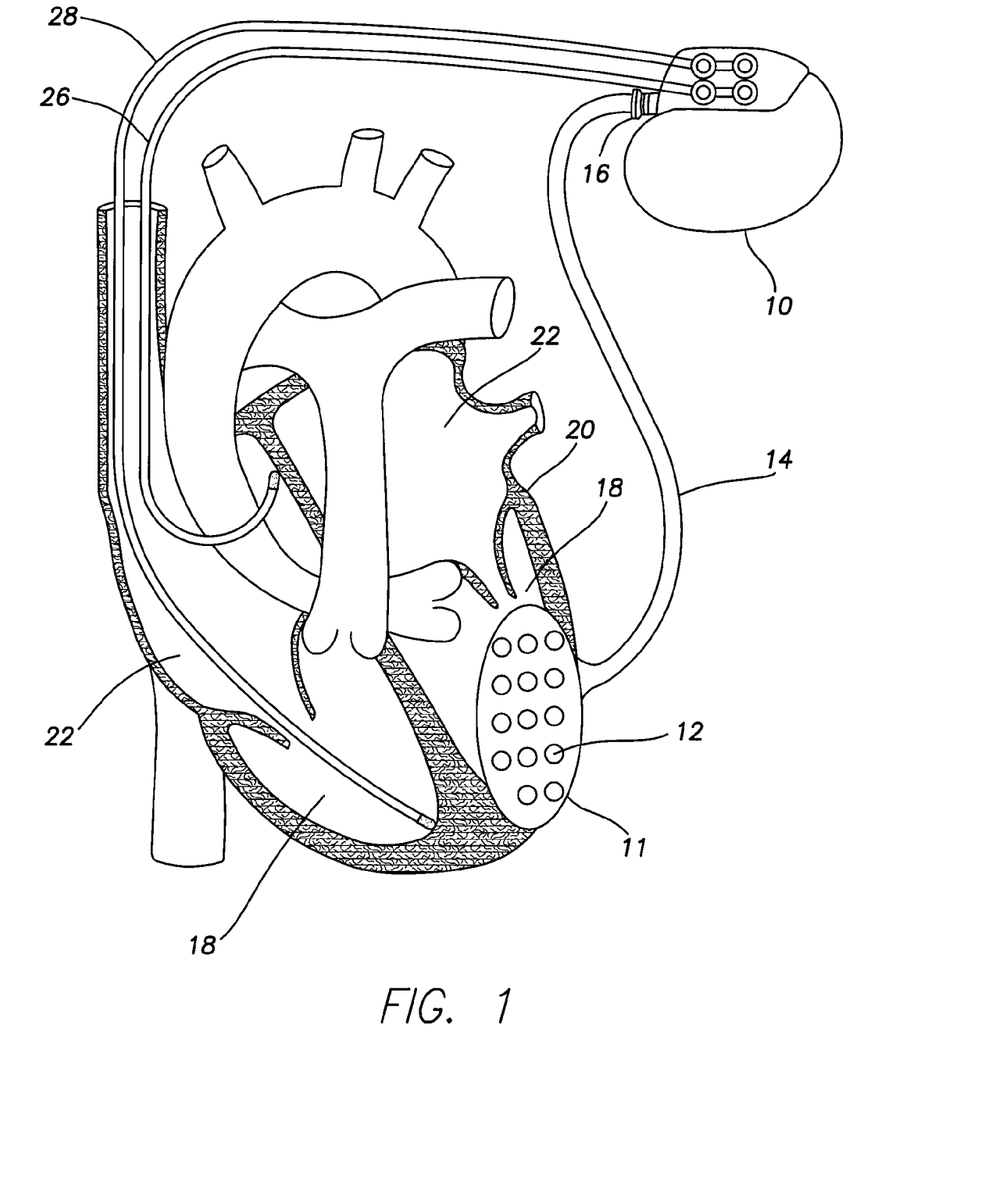
FIG. 1 illustrates an implantable device and a cardiac patch for monitoring and stimulating a patient's heart and formed in accordance with an embodiment.

FIG. 1 illustrates an implantable device 10 for monitoring and/or stimulating a heart 20 that is formed in accordance with an embodiment. The implantable device 10 is joined to a cardiac patch 11 attached to the heart 20 and capable of monitoring and/or pacing the heart 20 as explained in further detail below. A plurality of electrodes 12 are attached to the cardiac patch 11, such as, for example, being formed integral with the cardiac patch 11, being secured to a surface of the cardiac patch 11, being secured between adjacent layers of the cardiac patch 11, being embedded within the cardiac patch 11, and the like. The implantable device 10 is joined to a lead 14, and more specifically, to a connector 16 at an end of the lead 14. As shown in FIG. 1, the cardiac patch 11 is located on an external surface of the heart 20 at a ventricle 18, but may also be located at an atrium 22 of the heart 20, across both the ventricle 18 and the atrium 22, or otherwise. Alternatively, the cardiac patch 11 can be located across both ventricles 18 or across both atriums 22. Optionally, the electrodes 12 may be located on an internal surface of the heart 20. Alternatively, the electrodes 12 may be individually placed about the surface (internal or external) of the heart 20 and not as part of a common cardiac patch. Alternatively, multiple cardiac patches 10 and/or individual separate electrodes 12 may be used in combination. A variety of geometries may be used for the cardiac patch 11, examples of which are shown and described below in further detail.

Signals relating to the physiologic information or electrical characteristics of the heart 20 detected by the cardiac patch 11 are provided through the lead 14 to the implantable device 10. The implantable device 10 may constitute a monitoring module that monitors physiologic information and/or electrical characteristics of the heart 20 for a trend or a threshold to determine a current state or a health of the heart 20. The monitoring module may communicate with a separate therapy delivery module for pacing or providing electrical stimulation to the heart should predetermined criteria be met. The monitoring module may also communicate with an external health monitoring system, such as a system in a hospital or a person's home. In an alternative embodiment, the implantable device 10 may constitute a detection and therapy delivery module such as a pulse generator, a pacemaker, an implantable cardioverter defibrillator, a defibrillator, and the like. The implantable device 10 may be joined to an atrial lead 26 and/or a ventricular lead 28, which are connected to the heart 20, and the implantable device 10 may then provide an electrical stimulation through the atrial lead 26 and/or the ventricular lead 28 based on the physiological information detected by the cardiac patch 11. For example, stimulation may be provided when the intrinsic heartbeat is insufficient, when depolarization is not being conducted through the heart 20, when the heart rate is too slow to maintain an adequate blood flow to the body, and the like. Alternatively to, or in addition to, providing electrical stimulation through the leads 26, 28, the implantable device 10 may provide electrical stimulation through the electrodes 12 in the cardiac patch 11.

The implantable device 10 monitors the heart 20 of a patient and may measure electrical characteristics of the heart 20 of a patient to identify an abnormal heart condition based upon measurements in accordance with the processes described in copending U.S. patent application Ser. No. 11/470,564, titled "Method and Apparatus for Measurinq Physiologic Information Utilizing an Implantable Device", the complete subject matter of which is incorporated herein by reference in its entirety. For example, the implantable device 10 may detect when the patient is having an event, such as a post-myocardial infarct, "silent" myocardial infarcts, a myocardial infarct, an ischemia, a heart block, an arrhythmia, a fibrillation, a congestive heart failure, and the like. The cardiac patch 11 detects an electrical characteristic such as voltage, current, resistance, or impedance of cardiac tissue during a depolarization and repolarization of an inherent cardiac cycle. The electrical characteristics of the heart 20 are measured between one or more combinations of electrodes 12 to obtain a measured characteristic value. The electrical characteristics are indicative of a present physiological state of a portion of the heart 20 that is disposed substantially between the combination of electrodes 12, from which the electrical characteristic is detected. Based on the electrical characteristics of the heart 20, the implantable device 10 may subject the heart 20 to a preventative pacing scheme such as bi-ventricular, right ventricular, left ventricular, left atrial, right atrial, and bi-atrial pacing, or the implantable device 10 may subject the heart 20 to a defibrillation event.

In another embodiment, the cardiac patch 11 detects a deflection of cardiac tissue either during an inherent cardiac cycle or during cardiac pacing, and the implantable device 10 processes the amount of deflection, the frequency of the deflection, or other deflection characteristics to perform an appropriate pacing scheme or a defibrillation event. Additionally, by monitoring the excitability of cardiac tissue and its response to different pacing schemes, the implantable device 10 is able to provide a physician with information as to whether the hemodynamic functioning of a patient has improved, how scar formation is progressing, the status of local or global heart failure, and the like.

The implantable device 10 may include blocks of memory allocated to store electrical characteristics (e.g. both inherent cardiac cycle and pacing events), displacement characteristics (e.g. both inherent cardiac cycle and pacing events), baseline reference values, and/or physiological characteristics that are monitored by the electrodes 12 of the cardiac patch 11. The electrical characteristics may be voltage, current, resistance, and impedance measurements. The displacement characteristics may be measured position data from the sensor electrodes 12 that are stored over time. The baseline reference values may include reference characteristic values and reference displacement values that represent reference physiologic states and reference functional states, respectively. Reference values include initial electrical characteristics and initial displacement values from an initial cardiac cycle measurement that is taken when the cardiac patch 11 is first implanted in the pericardial space of a patient and/or during periodic checkups with a physician. The physiological characteristics are recorded over time and may include data relating to the current condition of the patient, e.g. whether the patient is suffering from a myocardial infarction, a post-myocardial infarction, a "silent" myocardial infarction, an ischemia, an arrhythmia, a heart block, a fibrillation, a congestive heart failure, and the like.

The implantable device 10 analyzes the electrical characteristics and/or displacement characteristics in combination with the reference values stored in the memory to determine if an abnormal heart condition exists. For example, the implantable device may compare the current measured electrical and displacement valves against reference values, and then classify the current measurement as a strong activation, a normal activation, a weak activation or a "no activation" condition. A strong activation may be identified when the measurement value is equal to the reference value during a cardiac pacing event. A normal activation may be identified when the measured value is approximately equal to the reference value during an inherent cardiac cycle (e.g., within +/−5% of the reference value). A weak activation may be identified when the measured value is less than the reference value. A weak activation may indicate the presence of scar tissue. A "No activation" condition may be identified when the measured value is substantially less than the reference value (e.g., less than 50% less than the reference value). When displacement measurements are being analyzed, a "no activation" condition is identified when the measured displacement value is a minimum displacement. A "no activation" condition indicates the presence of damaged cardiac tissue. Based on these characteristics, the implantable device 10 is able to determine the present physiological state of the heart 20, and when that certain states are determined, the implantable device 10 begins a pacing scheme or a defibrillation event.

Figure 2:
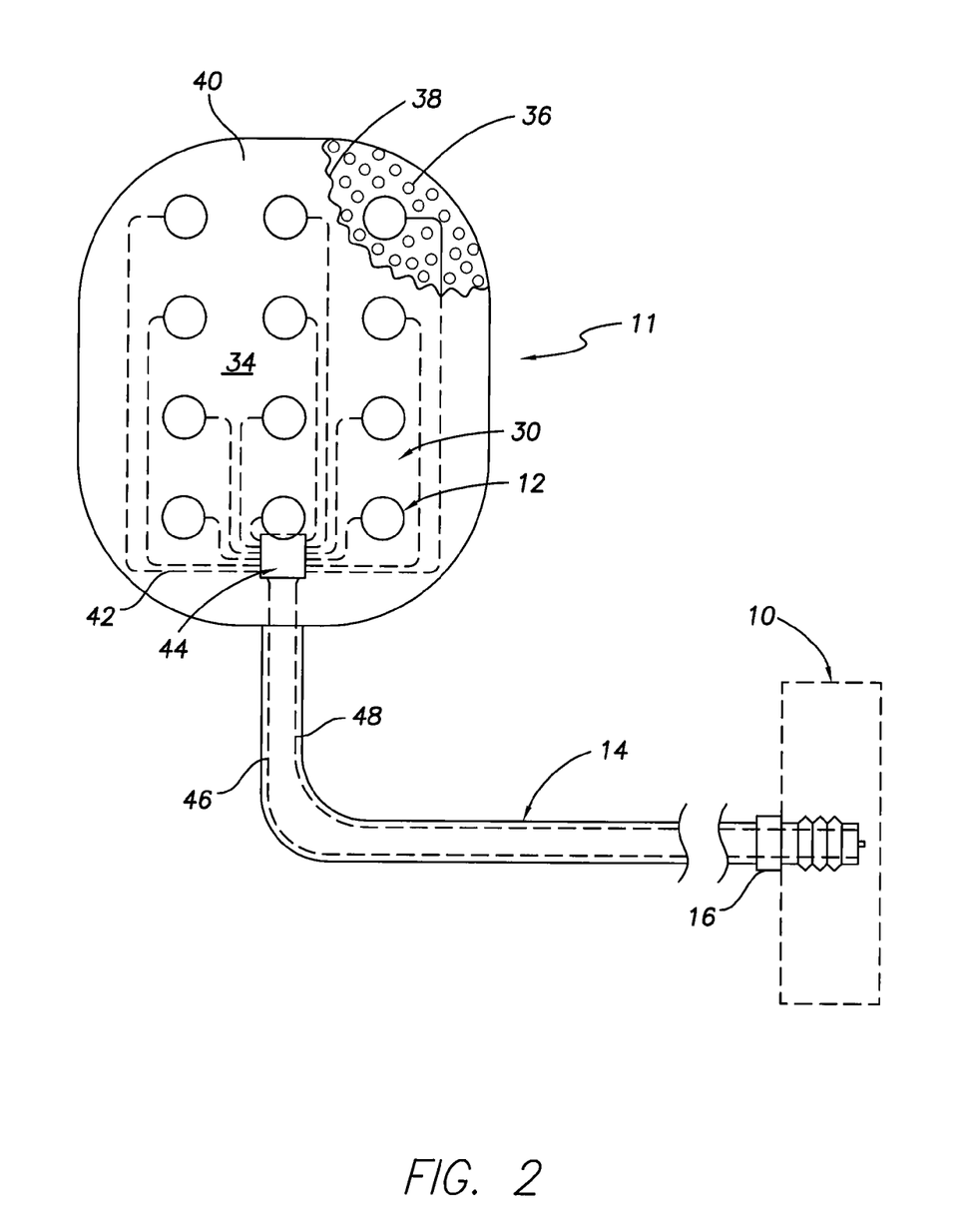
FIG. 2 illustrates the cardiac patch and a lead for use with the implantable device of FIG. 1 and formed in accordance with an embodiment.
Figure 3:
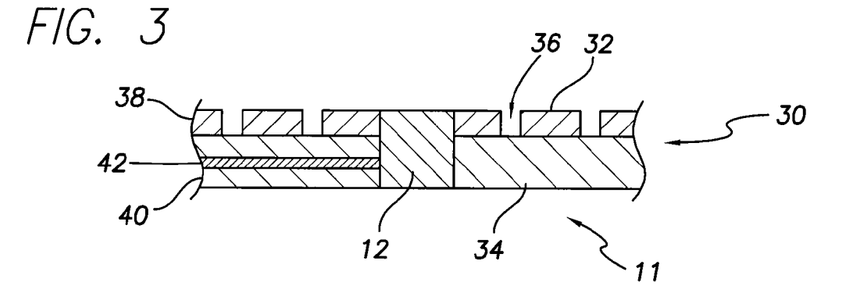
FIG. 3 illustrates a cross sectional view of the cardiac patch of FIG. 2.

FIG. 2 illustrates the cardiac patch 11 and lead 14 for the implantable device 10. FIG. 3 illustrates a cross sectional view of the cardiac patch 11 of FIG. 2. As illustrated in FIG. 3, the cardiac patch 11 represents a mesh patch and includes a body portion 30 having an inner surface 32, an outer surface 34 and a plurality of pores 36 extending into the body portion 30 from the inner surface 32. The inner surface 32 is the surface of the cardiac patch 11 that interfaces with the epicardial surface of the heart 20 (shown in FIG. 1). The outer surface 34 is opposite the inner surface 32. As indicated above, the pores 36 open to the inner surface 32 such that the pores 36 also interface with the epicardial surface of the heart 20. The pores 36 increase the adherence and compliance of the cardiac patch 11 to the epicardial surface of the heart 20 by allowing epicardial tissue to grow into or through the pores 36. The tissue ingrowth helps stabilize the cardiac patch 11 to the surface of the heart 20. The pores 36 are sufficiently sized and shaped to allow an adequate amount of tissue ingrowth to enhance the adherence of the cardiac patch 11 to the surface of the heart 20. Optionally, the pores 36 may be cylindrical, however, the shape of the pores 36 are not limited to a cylindrical shape. Optionally, the pores 36 may have angled walls, wherein the walls are angled outward from the inner surface 32 of the body portion 30. As such, the size of the opening is the smallest at the inner surface 32 and increases in size away from the inner surface 32. In this embodiment, the tissue ingrowth enhances the stabilization of the cardiac patch 11 to the surface of the heart 20. One optional size range of the pores 36 may be between approximately 1 to 5 millimeters wide; however other pore sizes may also allow an appropriate amount of tissue ingrowth.

Optionally, and as illustrated in FIG. 3, the body portion 30 may be made from multiple layers, such as an attachment layer 38 and a backing layer 40. Other layers may be provided in alternative embodiments to meet requirements for particular applications or to provide particular qualities or characteristics to the cardiac patch 11. For example, one layer may be formed of biocompatible material, while the other layer is formed of conductive material, such as a titanium or titanium alloy mesh, a platinum or platinum alloy mesh, a nickel or nickel alloy mesh, a conductive polymer such as a conductive silicone, and the like. Optionally, the conductive mesh may be used in combination with or in lieu of the electrodes 12 for measuring the electrical characteristics, such as impedance, of the heart 20. In another embodiment, the body portion 30 may be formed as an isodiametric surface directly on the electrodes 12.

The layers 38, 40 of the body portion 30 are fabricated using an injection molding process. Alternatively, other manufacturing or fabricating processes may be used. The layers 38, 40 are then joined to one another during the manufacturing process, such as by chemical bonding or by using a bonding agent. Alternatively, the layers 38, 40 may be joined during the molding process. The layers 38, 40 of the body portion 30 may be fabricated from the same materials, or alternatively, the layers 38, 40 may be fabricated from different materials. Materials for the layers 38, 40 may be selected from a group including at least one of polyester, polypropylene, polytetrafluoroethylene, polyurethane, silicone, silicone rubber, and the like. The type of material selected may depend on factors such as the materials softness, stiffness, pliability, flexibility, useful life, biocompatibility, adhesiveness, ability to allow tissue ingrowth, and other characteristics.

In the illustrated embodiment of FIG. 3, the pores 36 extend entirely through the attachment layer 38. The backing layer 40 however does not include any pores therein. As such, the backing layer 40 limits the amount of ingrowth of the heart tissue into the pores 36. Both of the layers 38, 40 include an opening for the electrode 12. As illustrated, the electrode 12 is embedded within the body portion 30 such that the electrode 12 is exposed at the inner surface 32. The electrode 12 is thus placed in close proximity to the epicardial surface of the heart 20 when the cardiac patch 11 is joined to the heart 20. Alternatively, the electrodes 12 may be placed on the outer surface 34 of the body portion 30, such that the electrodes 12 do not touch the epicardial surface of the heart 20. Regardless of the distance of the electrodes 12 from the epicardial surface, the electrodes 12 are positioned to monitor an electrical characteristic or a deflection of cardiac tissue during a depolarization and repolarization of the heart 20 and/or to provide an electrical stimulation to the heart 20.

As further illustrated in FIG. 3, an electrical conductor 42 is terminated to the electrode 12, and as illustrated in FIG. 2, the electrical conductor 42 is routed from the electrode 12 to the lead 14. Optionally, the electrical conductor 42 may be embedded within the backing layer 40 such that the electrical conductor 42 is not exposed along either the inner surface 32 or the outer surface 34. Alternatively, the electrical conductor 42 may be routed along one of the inner surface 32 or the outer surface 34.

Turning specifically to FIG. 2, each electrode 12 of the cardiac patch 11 includes a corresponding electrical conductor 42. Optionally, each of the electrical conductors 42 may be separately routed through the lead 14 to the connector 16. Alternatively, each of the electrical conductors 42 may be interconnected with an integrated circuit or processor 44 mounted in the cardiac patch 11. The processor 44 may include a microprocessor or multiplexing chip having a plurality of input points capable of receiving the electrical conductors 42 coming from each of the electrodes 12. The processor 44 also includes a lead output interconnected to an output conductor 46 extending through the lead 14. The lead output conductor 46 transmits data, such as electrical characteristics, deflection measurements, physiological characteristics and other data or control signals processed by processor 44 to the implantable device 10. The processor 44 also includes a lead input interconnected to an input conductor 48 extending through the lead 14. The input conductor 48 transmits data and/or power to the cardiac patch 11. Both the output conductor 46 and the input conductor 48 are interconnected to the implantable device 10 (shown in FIG. 1) by the connector 16. Alternatively, a single conductor may extend through the lead 14 interconnecting the implantable device 10 and the processor 44.

Figure 5:
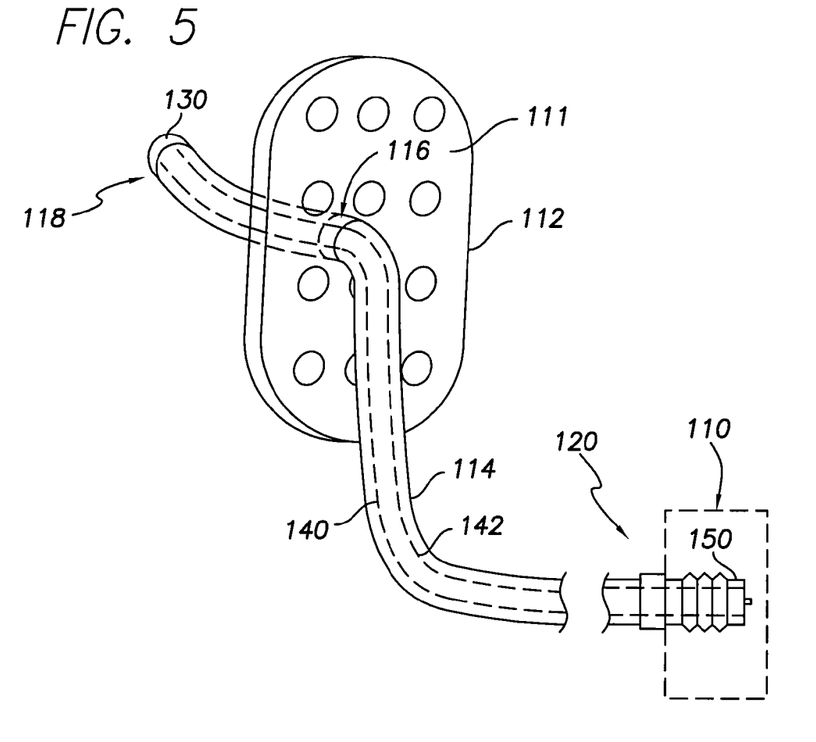
FIG. 5 illustrates a perspective view of a cardiac patch and lead formed in accordance with an alternative embodiment.

As further illustrated in FIG. 2, the lead 14 is connected to an outer edge of the cardiac patch 11, such as for example, being formed integral with the cardiac patch 11, being terminated at the cardiac patch 11, extending through a portion of the cardiac patch 11, being joined to a portion of the cardiac patch 11, being secured to a surface of the cardiac patch 11, being secured to an edge of the cardiac patch 11, being secured between adjacent layers of the cardiac patch 11, being embedded within the cardiac patch 11, and the like. In one embodiment, the lead 14 is connected to at least one of the inner surface 32 and the outer surface 34 remote from the outer edges of the cardiac patch 11, such as illustrated in FIG. 5, which will be discussed in further detail below.

The number and location of the electrodes 12 provided within the cardiac patch 11 depends on the application and surface area of the heart 20 to be covered. By way of example, the cardiac patch 11 may have as few as two electrodes 12 or as many as one-hundred, or more, electrodes 12. The electrodes 12 are fabricated from a conductive material, examples of which include a metal or metal alloy such as titanium, platinum, nickel and the like; a conductive polymer such as silicone; a biocompatible piezoceramics such as a lead zirconium titanate piezoceramic, a sodium potassium niobate piezoceramic, a bismuth sodium titanate piezoceramic, a bismuth potassium titanate piezoceramic, a barium titanate piezoceramic, and the like; a polyvinylidene fluoride piezopolymer; and the like. The electrodes 12 may be arranged in a pattern, such as a matrix pattern, having electrodes 12 spaced within the cardiac patch 11 at equal distances from one another in linear rows and columns. In another example, the electrodes 12 may be spaced at random, unequal distances from one another. Furthermore, the electrodes 12 may be utilized in either a unipolar or a bipolar configuration. Optionally, the electrodes 12 may represent monitoring or sensing electrodes or the electrodes 12 may represent stimulating electrodes used for pacing and/or defibrillation. Alternatively, the electrodes 12 may represent a combination of monitoring, sensing and stimulating electrodes, or each electrode 12 may have multiple uses of monitoring, sensing and stimulating. In one embodiment, the size, shape and positioning of the cardiac patch 11 and/or the number and positioning of the electrodes 12 may be selected depending on the type of monitoring or treatment needed. Optionally, the electrodes 12 may be arranged into groups to acquire information in groups, such that the electrical characteristic or deflection that occurs in one portion of the heart 20 can be compared and contrasted with another portion of the heart 20.

Figure 4:
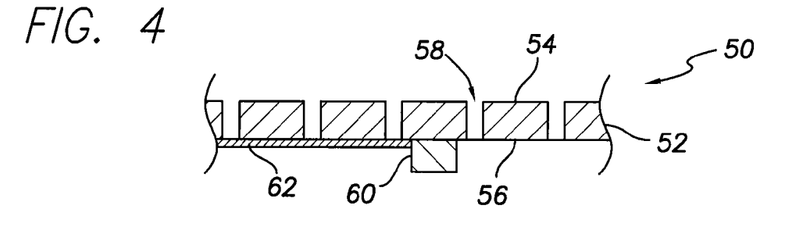
FIG. 4 illustrates a cross sectional view of a cardiac patch formed in accordance with an alternative embodiment.

FIG. 4 illustrates a cross sectional view of a cardiac patch 50 formed in accordance with an alternative embodiment. The cardiac patch 50 represents a mesh patch and includes a body portion 52 having an inner surface 54, an outer surface 56 and a plurality of pores 58 extending into the body portion 52 from the inner surface 54. In the illustrated embodiment, the pores 58 extend entirely through the body portion 52, and as such allow tissue growth entirely through the cardiac patch 50. Optionally, the tissue growth may continue beyond the outer surface 56 and possibly along the outer surface 56 to further enhance the attachment characteristics of the cardiac patch 50 to the surface of the heart 20 (shown in FIG. 1). Optionally, the body portion 52 may be made from multiple layers.

An electrode 60 is positioned along the outer surface 56 of the body portion 52. The electrode 60 is thus placed in close proximity to the epicardial surface of the heart 20 when the cardiac patch 50 is joined to the heart 20. Regardless of the distance of the electrode 60 from the epicardial surface, the electrode 50 is positioned to monitor an electrical characteristic or a deflection of cardiac tissue during a depolarization and repolarization of the heart 20 and/or to provide an electrical stimulation to the heart 20. An electrical conductor 62 is terminated to the electrode 60, and may be routed from the electrode 60 to a lead (not shown). Optionally, the body portion 52 mat be fabricated from a conductive material and may be electrically connect the electrode 60 and the heart 20.

FIG. 5 illustrates a perspective view of a cardiac patch 111 and a lead 114 formed in accordance with an alternative embodiment. The cardiac patch 111 includes a plurality of electrodes 112 arranged in a matrix. The cardiac patch 111 operates in a similar manner as the cardiac patch 11 shown in FIGS. 1-3. The cardiac patch 111 differs from the cardiac patch 11 in that the lead 114 is connected to the cardiac patch 111 in a different location than the lead 14 is connected to the cardiac patch 11. In the illustrated embodiment, the lead 114 is connected to the cardiac patch 11 at a connecting portion 116 of the lead 114. The connecting portion 116 is remote from both a distal end 118 and a proximal end 120 of the lead 114. Optionally, the connecting portion 116 is more closely positioned to the distal end 118 than the proximal end 120.

As illustrated in FIG. 5, the lead 114 represents a pericardial lead for pacing and/or defibrillating the heart. The pericardial lead 114 includes a lead electrode 130 embedded in the body of the pericardial lead 114. Optionally, multiple lead electrodes 130 may be embedded within the lead body. The lead electrode 130 is secured to the epicardial surface of the heart 20 (shown in FIG. 1) remote from the cardiac patch 111, and is utilized during pacing and/or defibrillation of the heart 20. Optionally, the lead 114 may be positioned along an exterior portion of the heart 20. Alternatively, the lead 114 may be positioned within an interior portion of the heart 20. The distal end 118 of the lead 114 is positioned along, and then secured to, the epicardial surface using known techniques. Additionally, the lead 114 is held in position using the cardiac patch 111. Once the cardiac patch 111 is secured to the heart 20, the lead 114 is fixed with respect to the heart 20 at the connecting portion 116.

An implantable device 110, represented schematically in FIG. 5, is joined to at least one lead electrode conductor 140 and at least one cardiac patch conductor 142. The lead electrode conductor 140 extends between a connector 150 and the lead electrode 130. The connector 150 is interconnected with the implantable device 110. As such, the lead electrode 130 is interconnected with the implantable device 110. The implantable device 110 may provide an electrical stimulation through the conductor 140 based on physiological information detected by the cardiac patch 111. For example, based on detected electrical characteristics of the heart 20, the implantable device 110 may subject the heart 20 to a preventative pacing scheme via the lead electrode 130, or the implantable device 110 may subject the heart 20 to a defibrillation event via the lead electrode 130.

The cardiac patch conductor 142 extends between the connector 150 and the cardiac patch 111. The cardiac patch conductor 142 thus interconnects the implantable device 110 and the electrodes 112 of the cardiac patch 111. Similar to the above described embodiments, the electrodes 112 may be any of monitoring electrodes, sensing electrodes, stimulating electrodes, or a combination thereof. Accordingly, the implantable device 110 is capable of stimulating the heart 20 using both a lead electrode 130 of a pericardial lead 114 and stimulating electrodes 112 of a cardiac patch. The combination of the electrodes 112 and 130 provide an efficient pacing scheme or defibrillation event.

Figure 6:
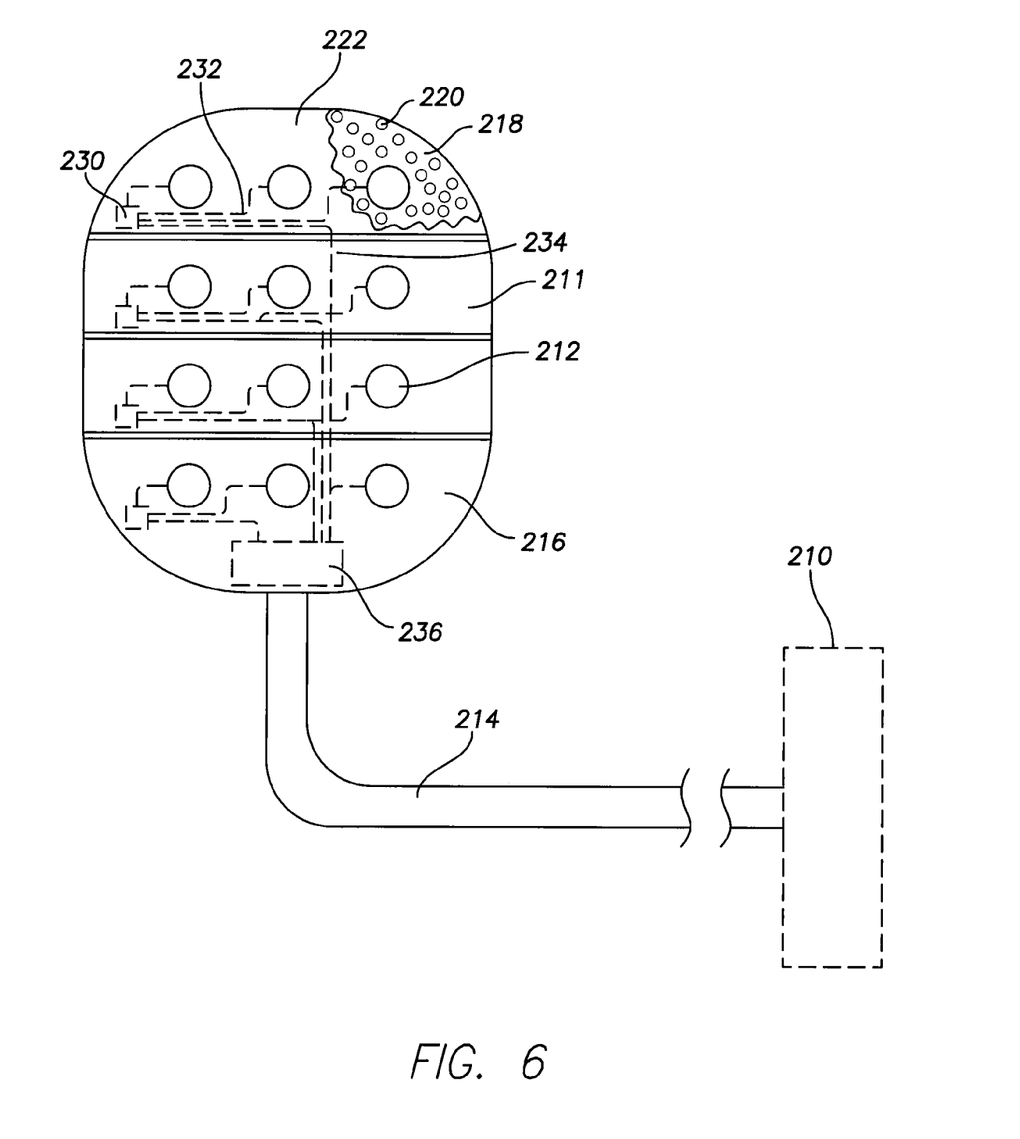
FIG. 6 illustrates a cardiac patch and lead formed in accordance with an alternative embodiment.

FIG. 6 illustrates a cardiac patch 211 and lead 214 formed in accordance with an alternative embodiment. The cardiac patch 211 includes a plurality of electrodes 212 arranged in a matrix. The cardiac patch 211 operates in a similar manner as the cardiac patch 11 shown in FIGS. 1-3. The cardiac patch 211 differs from the cardiac patch 11 in that the cardiac patch 211 is formed from multiple printed circuit boards 216. The electrodes 212 are electrically connected to the printed circuit boards 216, and in some embodiments, may be embedded within the printed circuit boards 216. The printed circuit boards 216 are flexible and conform to the shape of the heart 20 (shown in FIG. 1) at the area of attachment. The flexible printed circuit boards 216 form a backing layer of the cardiac patch 211 that is joined to an attachment layer 218. The attachment layer 218 includes a plurality of pores 220 that allow ingrowth of the cardiac tissue for securing the cardiac patch 211 to the heart 20.

Optionally, each of the printed circuit boards 216 are interconnected by flexible connecting portions 222. In one embodiment, the connecting portions 222 are continuations of the attachment layer 218 such that a single attachment layer 218 is provided and multiple printed circuit boards 216 are joined to the attachment layer 218. Alternatively, the connecting portions 222 may be a separate layer that is joined between adjacent attachment layers 218, adjacent printed circuit boards 216, or both. Optionally, the connecting portion 222 may contact the surface of the heart 20. Alternatively, the connecting portions 222 may be elevated from the surface of the heart 20. The connecting portions 222 allow relative movement between the printed circuit boards 216 once the cardiac patch 211 is secured to the heart 20. For example, the connecting portions 222 allow for normal expansion and contraction of the epicardial surface of the heart. In one embodiment, the electrodes 212 may be attached to the connecting portions 222.

Optionally, a width of the connecting portions 222 is substantially narrower than a width of the printed circuit boards 216. As such, the printed circuit boards 216 remain relatively close to one another and the printed circuit boards 216 may monitor a common area of the heart 20, such as the same atrium or the same ventricle. Alternatively, the width of the connecting portions 222 may be approximately equal to the width of the printed circuit boards 216 or substantially wider than the width of the printed circuit boards 216. As such, the multiple printed circuit boards 216 may be spaced apart from one another and may be positioned on different areas of the heart 20. For example, in one embodiment, a single printed circuit board 216 may be positioned on each of the right atrium, left atrium, right ventricle and left ventricle. As such, each of the areas of the heart 20 may be monitored and/or treated with electrical stimulation with a single cardiac patch 211. In another alternative embodiment, no connecting portion may be used between each printed circuit board 216, such that each printed circuit board 216 may be independently positioned on the surface of the heart. However, conductors (not shown) would be provided to interconnect each printed circuit board 216 with the lead 214. For example, multiple, individual cardiac patches 211 may be interconnected with a common lead 214. Additionally the individual cardiac patches 211 may be interconnected with one another.

Each of the printed circuit boards 216 include an integrated circuit or processor 230 thereon and a trace 232 extending between the processor 230 and each electrode 212 associated with the printed circuit board 216. Optionally, a portion of the trace 232 may define the electrode 212. Each processor 230 includes a conductor or trace that operates as a primary conductor 234. The primary conductor 234 extends across the connecting portion 222 and may connect to a primary processor 236 on one of the printed circuit boards 216. The primary processor 236 is interconnected to an implantable device 210, which is represented schematically in FIG. 6, through a conductor (not shown) in the lead 214. As such, each of the electrodes 212 are interconnected to the implantable device 210 via the conductor, the primary processor 236, the primary conductor 234, the processor 230 and the trace 232. Optionally, the processor 230 and the trace 232 may be embedded within the printed circuit board 216. Alternatively, the processor 230 and the trace 232 may be positioned between the printed circuit board 216 and the attachment layer 218. Alternatively, the processor 230 and the trace 232 may be positioned on the outer surface of the printed circuit board 216, opposite the attachment layer 218.

Figure 7:
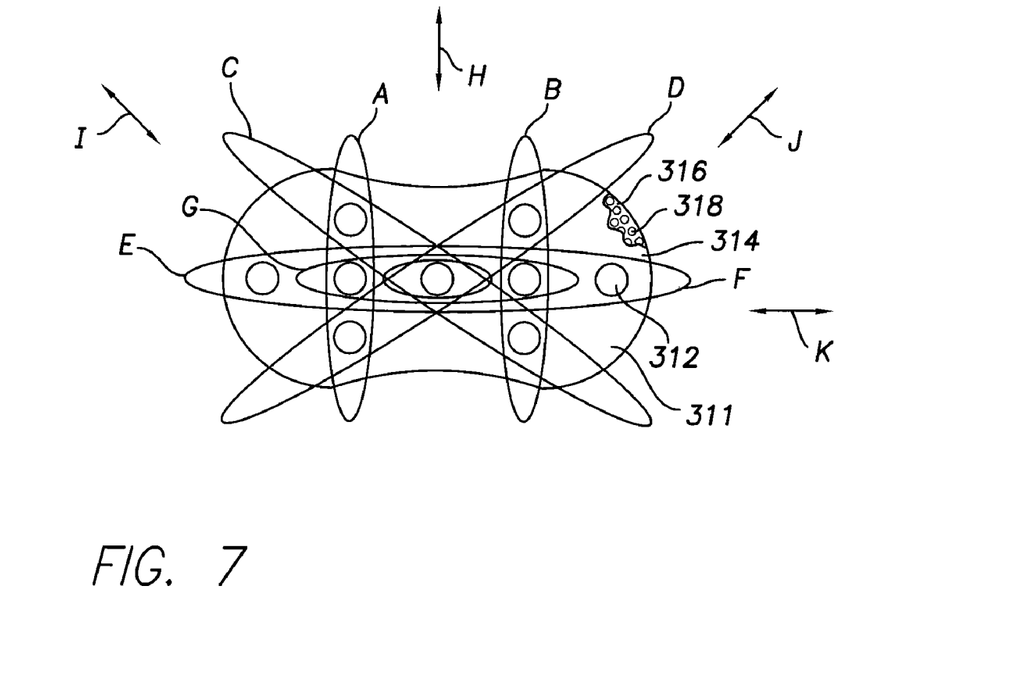
FIG. 7 illustrates a cardiac patch utilized in accordance with an alternative embodiment and shows an exemplary pacing scheme for the cardiac patch.

FIG. 7 illustrates a cardiac patch 311 utilized in accordance with an alternative embodiment and shows an exemplary pacing scheme for the cardiac patch 311. The cardiac patch 311 has an hour-glass shape with bulbous end portions and a narrower mid-portion. The cardiac patch 311 includes a backing layer 314 and an attachment layer 316 having multiple pores 318. The cardiac patch 311 also includes multiple electrodes 312 arranged in a pattern such that each electrode 312 is included in more than one electrode group. Each electrode group includes electrodes 312 that are linearly aligned with one another. The electrode groups are circled and identified with letters A-G. The circles identifying the groups do not form a part of the cardiac patch 311. Additionally, other combinations may be available to form more groups than the groups A-G. Additionally, more groups may be available when more electrodes 312 are provided.

In the illustrated embodiment, the electrodes 312 in each of electrode groups A and B extend linearly along paths parallel to arrow H; the electrodes 312 in the electrode group C extend linearly along a path parallel to arrow I; the electrodes 312 in the electrode group D extend linearly along a path parallel to arrow J; and the electrodes 312 in each of electrode groups E, F and G extend linearly along paths parallel to arrow K. Arrows H and K are perpendicular to each other and arrows I and J are oblique with respect to both arrows H and K. By monitoring the physiologic information or electrical characteristics of the heart 20 in multiple directions, a more comprehensive analysis of the heart 20 may be made.

Figure 8:
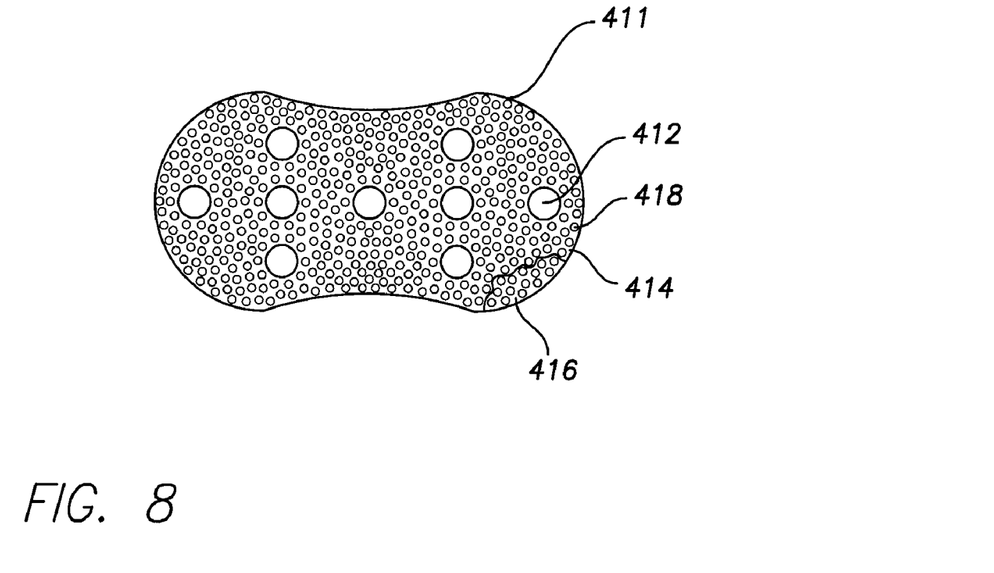
FIG. 8 illustrates a cardiac patch utilized in accordance with an alternative embodiment.

FIG. 8 illustrates a cardiac patch 411 utilized in accordance with an alternative embodiment. Multiple electrodes 412 are embedded within the cardiac patch 411 and arranged in a pattern. Alternatively, the electrodes may be attached to one of the surfaces of the cardiac patch 411. The cardiac patch 411 has an hour-glass shape with bulbous end portions and a narrower mid-portion. The cardiac patch 411 defines a mesh patch and includes a backing layer 414 and an attachment layer 416 having multiple pores 418. In the embodiment illustrated in FIG. 8, the pores 418 extend entirely through the cardiac patch 411. For example, the pores 418 in each layer are aligned during joining of the layers. Alternatively, the pores 418 may be formed after the layers are joined to one another. Optionally, the cardiac patch 411 may be a single layer.

Figure 9:
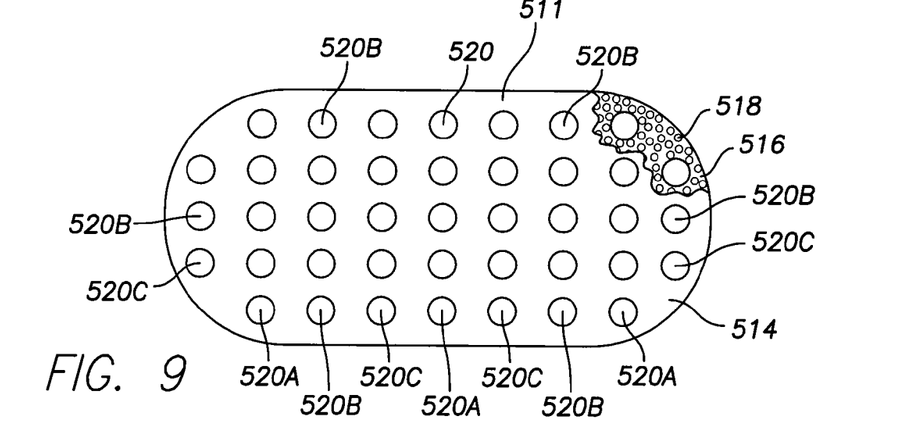
FIG. 9 illustrates a cardiac patch utilized in accordance with an alternative embodiment.

FIG. 9 illustrates a cardiac patch 511 utilized in accordance with an alternative embodiment. The cardiac patch 511 has an oval shape and includes a backing layer 514 and an attachment layer 516 having multiple pores 518. The cardiac patch 511 also includes multiple electrodes 520 arranged in a pattern. In the illustrated embodiment, the cardiac patch 511 is used to monitor the electrical characteristics of the heart 20; to measure positional characteristics of the heart 20, such as the expansion and contraction of the heart 20; and to provide therapy to the heart 20, such as through electrical stimulation. To accomplish each of these functions, the cardiac patch 511 includes different types of electrodes 520, and each electrode functions in a single role.

The cardiac patch 511 includes monitoring electrodes 520A that monitor the electrical characteristics. The monitoring electrodes 520A detect an electrical characteristic such as voltage, current, resistance, or impedance of cardiac tissue during a depolarization and repolarization of the cardiac cycle. The cardiac patch 511 includes displacement sensors 520B that cooperate to sense changes in the physical distances and/or orientations between each of the displacement sensors 520B. For example, as the heart progresses through systolic and diastolic states, the distance and/or orientation between a first set of the sensors 520B may expand and contract by a first amount. Similarly, the distance and/or orientation between a second set of the sensors 520B may change, but not necessarily by the same amount or to the same degree as the changes in distance and/or orientation between the first set of sensors 520B. These changes in distances and/or orientations may be used by an implantable device (not shown) to determine a current state or a health of the heart 20. The cardiac patch includes stimulating electrodes 520C that are used to provide electrical stimulation to the heart 20 for pacing and/or defibrillation. The arrangement of the electrodes 520A, 520B and 520C may be varied depending on the type of cardiac patch 511 used or the particular application. Optionally, the electrodes 520A, 520B and 520C may be arranged in rows. Alternatively, the electrodes 520A, 520B and 520C may be randomly positioned.

Figure 10:
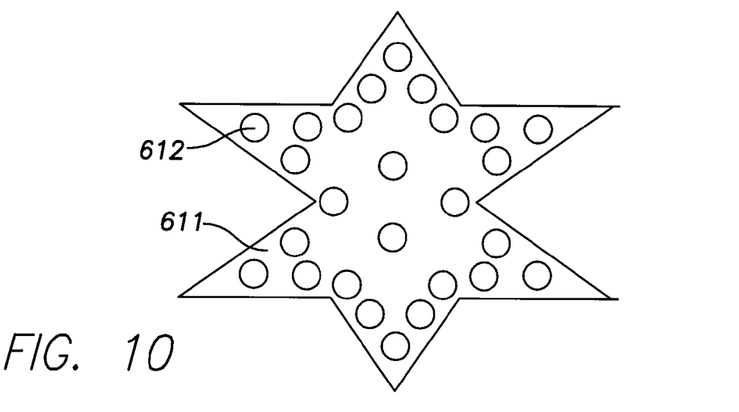
FIG. 10 illustrates a cardiac patch utilized in accordance with an alternative embodiment.
Figure 11:
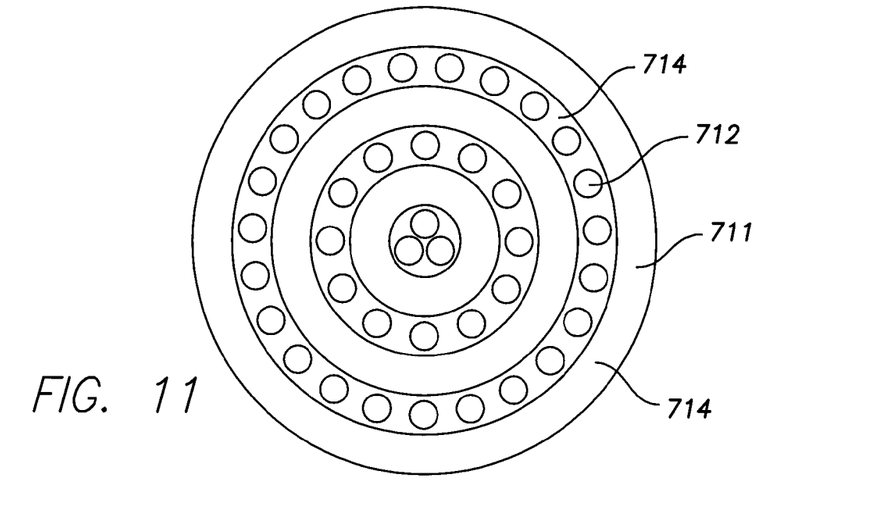
FIG. 11 illustrates a cardiac patch utilized in accordance with an alternative embodiment.

FIGS. 10 and 11 illustrate cardiac patches 611 and 711, respectively, having alternative shapes and sizes than the previously described cardiac patches. FIG. 10 shows a cardiac patch 611 with an irregular polygon shape and having the plurality of electrodes 612 spaced at irregular distances from one another. FIG. 11 shows a cardiac patch 711 including a circular shape and having a plurality of concentric rings 714 with electrodes 712 spaced at equal distances from each other within each concentric ring 714. Optionally, a plurality of pores (not shown) may extend through the cardiac patch 711 within the concentric rings 714 that do not include the electrodes 712.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. An implantable cardiac patch configured to be joined to a surface of a heart, the device comprising:
   a body portion having an inner surface configured to be joined to the surface of the heart, the body portion having a plurality of pores extending into the body portion from the inner surface;
   a plurality of electrodes attached to the body portion; and
   a lead electrically connected to the electrodes at a connecting portion of the lead, the lead having a proximal end configured for joining to an implantable device;
   wherein the body portion includes a backing layer comprising a flexible printed circuit board having traces thereon that extend to the electrodes.

2. The cardiac patch of claim 1, wherein the pores extend completely through the body portion.

3. The cardiac patch of claim 1, wherein the pores extend completely through an inner layer of the body portion and the pores are covered by an outer layer of the body portion.

4. The cardiac patch of claim 1, wherein the pores are circular.

5. The cardiac patch of claim 1, wherein the pores are sized and shaped to allow ingrowth of the heart tissue at least partially into the pores to substantially increase the adherence of the body portion to the surface of the heart.

6. The cardiac patch of claim 1, wherein the body portion comprises a material selected from a group consisting of at least one of polyester, polypropylene, polytetrafluoroethylene, polyurethane, silicone, and silicone rubber.

7. The cardiac patch of claim 1, wherein the body portion further includes an attachment layer, and the pores are included in the attachment layer.

8. The cardiac patch of claim 1, wherein the electrodes include at least one of a monitoring electrode, a sensing electrode and a pacing electrode.

9. The cardiac patch of claim 1, wherein a distal end of the lead includes the connecting portion and is attached to the body portion.

10. The cardiac patch of claim 1, wherein a distal end of the lead includes a lead electrode.

11. An implantable cardiac patch configured to be joined to a surface of a heart, the device comprising:
    a body portion having an inner surface configured to be joined to the surface of the heart, the body portion having a plurality of pores extending into the body portion from the inner surface;
    a plurality of electrodes attached to the body portion; and
    a lead electrically connected to the electrodes at a connecting portion of the lead, the lead having a proximal end configured for joining to an implantable device;
    wherein the body portion includes a backing layer comprising multiple printed circuit boards interconnected by a mesh layer comprising the pores, each printed circuit board having traces thereon that extend to at least one of the electrodes.

12. The cardiac patch of claim 11 further comprising a plurality of processors, at least one processor on each of the printed circuit boards and connected to at least one of the electrodes.

13. An implantable cardiac patch configured to be joined to a surface of a heart, the device comprising:
    a body portion having an inner surface configured to be joined to the surface of the heart, the body portion having a plurality of pores extending into the body portion from the inner surface;
    a plurality of electrodes attached to the body portion; and
    a lead electrically connected to the electrodes at a connecting portion of the lead, the lead having a proximal end configured for joining to an implantable device;
    wherein the body portion includes a backing layer comprising a flexible printed circuit board having the electrodes embedded therein.

14. An implantable cardiac patch configured to be joined to a surface of a heart, the device comprising:
    a body portion having an inner surface configured to be joined to the surface of the heart, the body portion having a plurality of pores extending into the body portion from the inner surface;
    a plurality of electrodes attached to the body portion; and
    a lead electrically connected to the electrodes at a connecting portion of the lead, the lead having a proximal end configured for joining to an implantable device;
    wherein the body portion comprises: an attachment layer having the plurality of pores extending there through; and a backing layer joined to the attachment layer, the backing layer comprising a flexible printed circuit board carrying the electrodes.

15. An implantable cardiac patch configured to be joined to a surface of a heart, the device comprising:
    a body portion having an inner surface configured to be joined to the surface of the heart, the body portion having a plurality of pores extending into the body portion from the inner surface;
    a plurality of electrodes attached to the body portion; and
    a lead electrically connected to the electrodes at a connecting portion of the lead, the lead having a proximal end configured for joining to an implantable device;
    wherein the body portion comprises a backing layer having a plurality of printed circuit boards interconnected by flexible connecting portions that allow for relative movement of the printed circuit boards.

16. The cardiac patch of claim 15 wherein the widths of the connecting portions are substantially narrower than the widths of the printed circuit boards.

17. The cardiac patch of claim 15 wherein the widths of the connecting portions are approximately equal to or wider than the widths of the printed circuit boards.

* * * * *